(12) United States Patent
Bruegger et al.

(10) Patent No.: US 8,477,026 B2
(45) Date of Patent: Jul. 2, 2013

(54) MEDICAL DATA TRANSMISSION SYSTEM (75) Inventors: Martin Bruegger, Bern (CH); Bernd Roesicke, Mannheim (DE); Markus Oberli, Kirchberg (CH); Stefan Lindegger, Huttwil (CH)

(73) Assignees: Roche Diagnostics Operations, Inc., Indianapolis, IN (US); Roche Diagnostics International AG, Rotkreuz (CH)

( * ) Notice: Subject to any disclaimer, the term of this patent is extended or adjusted under 35 U.S.C. 154(b) by 937 days.

(21) Appl. No.: 12/556,309

(22) Filed: Sep. 9, 2009

(65) Prior Publication Data
US 2010/0141429 A1    Jun. 10, 2010

Related U.S. Application Data (63) Continuation of application No. PCT/EP2008/001637, filed on Mar. 1, 2008.

(30) Foreign Application Priority Data

Mar. 9, 2007  (EP) .................................... 07004859

(51) Int. Cl.
*G08B 1/08* (2006.01)
*G08B 23/00* (2006.01)
*A61B 5/00* (2006.01)

(52) U.S. Cl.
USPC ................... 340/539.12; 340/539.1; 340/506; 340/531; 340/573.1; 600/301; 600/316; 128/903; 128/904

(58) Field of Classification Search
USPC .................................................. 340/539.12
See application file for complete search history.

(56) References Cited

U.S. PATENT DOCUMENTS

| 4,622,979 | A | 11/1986 | Katchis et al. |
| 4,883,064 | A | 11/1989 | Olson et al. |
| 4,944,304 | A | 7/1990 | Nishina |
| 6,014,578 | A | 1/2000 | Minoz |
| 6,434,429 | B1 | 8/2002 | Kraus et al. |

(Continued)

FOREIGN PATENT DOCUMENTS

| DE | 102004020160 A1 | 11/2005 |
| EP | 0113379 B1 | 7/1984 |

(Continued)

*Primary Examiner* — Donnie Crosland
(74) *Attorney, Agent, or Firm* — Roche Diagnostics Operations, Inc.

(57) ABSTRACT

A system for transmission of medical data comprises a first device which is designed to be worn on the body of a patient and which generates medically relevant data when in operation, said data being transmitted wirelessly to a second device. The first device comprises a communication unit for the wireless communication with the second device, a circuit which generates medically relevant data when in operation and a handover memory for the intermediate storage of data that are to be transferred from the circuit to the communication unit or from the communication unit to the circuit. The data generating circuit is connected to the handover memory via a first data line and the communication unit is connected to the handover memory via a second data line. The first device comprises a change-over switch closing the first data line and interrupting the second data line in a first switched state and interrupting the first data line and closing the second data line in a second switched state, said change-over switch changing between the first and second switched state without communication with the data generating circuit.

13 Claims, 4 Drawing Sheets

U.S. PATENT DOCUMENTS

| | | |
|---|---|---|
| 6,571,128 B2 | 5/2003 | Lebel et al. |
| 7,188,034 B2 | 3/2007 | Staib et al. |
| 2003/0130590 A1 | 7/2003 | Bui et al. |
| 2003/0225319 A1* | 12/2003 | Ford et al. ............. 600/300 |
| 2004/0171921 A1* | 9/2004 | Say et al. ............. 600/347 |
| 2006/0253045 A1 | 11/2006 | Coifman |
| 2006/0253067 A1 | 11/2006 | Staib et al. |
| 2006/0281454 A1 | 12/2006 | Gray |

FOREIGN PATENT DOCUMENTS

| | | |
|---|---|---|
| EP | 1062985 A2 | 12/2000 |
| EP | 1302875 A1 | 4/2003 |
| EP | 0978254 B1 | 2/2005 |
| EP | 1702559 A2 | 9/2006 |
| WO | 2006/102086 A1 | 9/2006 |
| WO | 2006/133851 A2 | 12/2006 |

* cited by examiner

MEDICAL DATA TRANSMISSION SYSTEM

REFERENCE

This application is a continuation of PCT/EP2008/001637 filed 1 Mar. 2008 which is based on and claims priority to European Patent Application No. EP 07 004 859.0 filed 9 Mar. 2007, which are hereby incorporated by reference.

FIELD

This disclosure relates to a medical data transmission system

BACKGROUND

A data transmission system of this type comprises at least two devices. According to its purpose, a first device is carried on the body by a patient and, in operation, generates medically relevant data that are transmitted to a second device in a wireless manner. The first device typically is a measuring device that uses a sensor in or on the body of a patient to make measurements and generates measuring data as medically relevant data that are transmitted to the second device. However, the first device can just as well be a treatment device, for example an infusion device that administers a medical agent, in particular insulin. The medically relevant data that are generated by a treatment device of this type typically are treatment data, for example infusion rates or similar data.

The second device of a medical data transmission system of this type typically serves for display, analysis of the medically relevant data generated by the first device and/or control of the first device.

In the first device, the medically relevant data are generated by a circuit, which contains, for example, a sensor for in-vivo measurement of an analyte concentration, and are transmitted to the second device by an internal communication unit in a wireless manner. The data generated by the circuit is initially stored in a handover memory from which they can be read-out by the communication unit. It is therefore necessary for both the data-generating circuit and the communication unit to have access to the handover memory. In order to avoid collisions, known data transmission systems with direct access (random access) to data have defined access rules and control mechanisms.

WO 2006/133851 A2 teaches the use of a handover memory in a medical data transmission system, which handover memory has a separate data input and data output each for the circuit and the communication unit. Although simultaneous access to the handover memory by the circuit and the communication unit is unlikely, it can lead to significant problems in particular if predefined protocols for communication with the second device, for example Bluetooth, are used.

Asynchronous communication processes involving access of different system components to a common memory must therefore be expected to be associated with a higher probability of data corruption. This necessitates a greater effort for safeguarding data, for example the use of buffer memories for short-term temporary data storage, and, in addition, a higher level of coordination and control between the participating system components.

It is known from U.S. Pat. No. 6,571,128 B2 to prevent access conflicts of the data-generating circuit and the communication unit of a medical data transmission system with regard to a common memory in that the data-generating circuit contains a microprocessor as master and the communication unit contains another microprocessor as slave. Although access conflicts can be precluded by this means, access of the communication unit to the handover memory is possible only in a restricted manner. Another disadvantage is that, in the case of a master processor defect, the microprocessor of the communication unit usually can no longer access the handover memory at all and, as a consequence, all data stored in the handover memory are lost. This is particularly serious if data are transmitted only relatively rarely, for example at intervals of approximately one week, from the first device to the second device.

SUMMARY

Therefore embodiments of the invention to devise a way, in which the access options of the communication unit of a medical data transmission system with regard to a handover memory can be improved without increasing the level of the coordination and control needs between the participating system components.

In a data transmission system according to the disclosure, there is no need for synchronization or coordination of the data-generating circuit and the communication unit. Since, accordingly, no control signals need to be exchanged between the data-generating circuit and the communication unit, a system according to the invention can be implemented with advantageously low effort with regard to hardware, protocol software, project organization, and evaluation.

The data-generating circuit and the communication unit of a data transmission system are connected to the handover memory by means of a first data line and a second data line, respectively. A changeover switch closes the first data line and interrupts the second data line in a first switching state such that only the data-generating circuit can access the handover memory in the first switching state. In a second switching state of the changeover switch, the first data line is interrupted and the second data line is closed such that only the communication unit can access the handover memory. In the process, the changeover switch switches between the first and the second switching state without communicating with the data-generating circuit. By this means, it is feasible to preclude any influence of the data-generating circuit on the communication unit and thus create a true alternative to known master-slave architectures. It is particular to a data transmission system according to the invention that the access of the communication unit to the handover memory, and therefore to the medically relevant data that are to be transmitted to the second device, is not restricted by the data-generating circuit.

The changeover switch can be actuated by the communication unit and in some embodiments by the communication unit exclusively. If the communication unit needs to have access to the handover memory, for example in order to provide medically relevant data that have been collected by the data-generating circuit and are requested by the second device, the communication unit actuates the changeover switch and thereby transitions it from its first switching state to the second switching state. Once the communication unit has read-out the needed data from the handover memory and therefore needs to have no further access to the handover memory for the time being, the communication unit again actuates the changeover switch and thereby transitions it back to the first switching state, in which only the data-generating circuit has access to the memory. It is feasible just as well to provide the changeover switch such that it returns to the first switching state in a self-actuated manner if the communication unit fails to access the handover memory for a predefined number of clock cycles.

In order to prevent any influence of the data-generating circuit on the communication unit, the switch can just as well cycle between its switching states in a self-actuated manner, for example by being actuated by an independent random access processor and thus providing the data-generating circuit and the communication unit access to the handover memory in an alternating manner.

Since the changeover switch switches between the first and the second switching state without communicating with the data-generating circuit, write and read operations of the data-generating circuit may be interrupted and thus disturbed. Accordingly, the data written to the handover memory by the data-generating circuit may be corrupted, incomplete or contain errors. As a counter-measure addressing the associated problem, the data-generating circuit can, for example, contain a microprocessor that repeats write or read operations that have been interrupted by switching operations and has its own memory, in which data can be stored temporarily prior to transmission to the handover memory. By this means, the memory of the data-generating circuit can be read-out again and its content can be transmitted to the handover memory in case a write operation was interrupted.

Another option that is well-suited in particular for measuring devices that deliver measuring data in short time intervals, for example, of one minute, in the scope of a so-called "continuous monitoring", is to ignore failed write operations, since individual measuring values or even series of measuring values over several minutes that are lost due to interrupted write operations can be interpolated during a subsequent analysis.

BRIEF DESCRIPTION OF THE DRAWINGS

Further details and advantages of invention embodiments are illustrated based on exemplary embodiments and by making reference to the appended drawings. The features described can be made the subject matter of claims either alone or in combination. Identical and equivalent components are identified by consistent reference numbers. In the figures:

DETAILED DESCRIPTION

Figure 1:
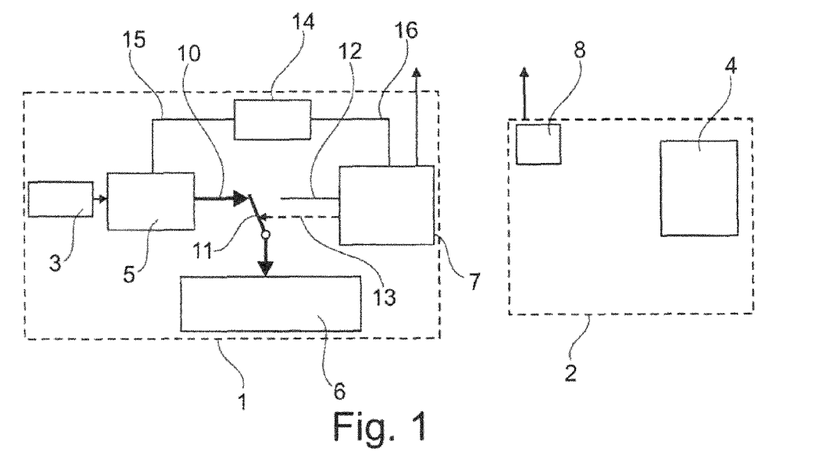
FIG. 1 shows a schematic view of an embodiment of a medical data transmission system collecting medically relevant data.

The medical data transmission system shown in FIG. 1 comprises a first device 1, which is designed to be worn on the body by a patient and, in operation, generates medically relevant data that are transmitted to a second device 2 in a wireless manner. In the exemplary embodiment shown, the first device 1 is a measuring device with an implantable sensor 3 for in-vivo measurement of an analyte concentration, for example of the glucose concentration, in the body of a patient. The second device 2 is a display device that has an output facility 4 for output of measured analyte concentrations, for example a display.

The first device 1 contains a communication unit 7 that contains a transmitter, a receiver, and a microprocessor for controlling the communication with the second device 2. Likewise, the second device 2 also contains a communication unit 8 that contains a transmitter, a receiver, and a microprocessor for controlling the communication with the first device 1.

The medically relevant data are generated in the first device as measuring data by means of a circuit that contains a microprocessor 5 in addition to the sensor 3. The microprocessor 5 controls the primary function of the first device 1 which, in the example shown, is the generation of measuring data, but can, for example, just as well be a treatment of the patient, for example by administering an agent. Therefore, the microprocessor 5 of the data-generating circuit is also called system processor in this application. The data-generating circuit 3, 5 and the communication unit 7 each are connected to a power source 14, for example a battery, by means of separate supply lines 15, 16. Said power source 14 cannot be turned off by either the data-generating circuit 3, 5 or by the communication unit 7.

In the embodiment shown, analog sensor signals, for example current amplitudes that are correlated to the measuring value of interest, are digitized by an analog-digital converter of the microprocessor 5, and subjected to a pre-analysis. In said pre-analysis, the digitized raw data of the sensor 3, which are determined in first time intervals of, for example, 1 second, are compressed and used to generate measuring data for second time intervals of, for example, 1 min. Data compression can be effected, for example, by averaging or, just as well, by more complicated procedures of data processing or compression, such as are described, for example, in EP 1702559 A2 or DE 102004020160 A1.

The measuring data generated by the microprocessor 5 are stored in a handover memory 6 to which the microprocessor 5 is connected by means of a first data line 10. In said first data line 10, there is a changeover switch 11 that is shown in its first switching state in FIG. 1, in which it closes the first data line 10 such that the data-generating microprocessor 5 can write measuring data to the handover memory 6 as medically relevant data.

The handover memory 6 is connected to the communication unit 7 of the first device 1 by means of a second data line 12. The second data line 12 is interrupted in the first switching state of the changeover switch 11 that is shown in FIG. 1 such that the communication unit 7 cannot access the handover memory 6. In the exemplary embodiment shown, the changeover switch 11 is actuated exclusively by the communication unit 7 or to be more precise, exclusively by the microprocessor contained in the communication unit 7. For this purpose, the communication unit 7 is connected to the changeover switch by means of a control line 13. In case of need, the communication unit 7 gains access to the handover memory 6 by actuating it by means of a signal via the control line 13 and transitioning it from the first switching state shown in FIG. 1 to the second switching state shown in FIG. 2.

Figure 2:
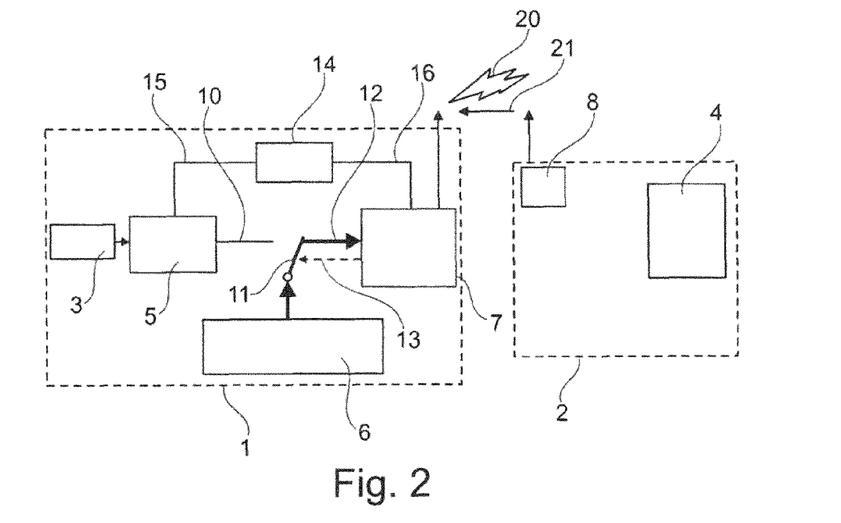
FIG. 2 shows the embodiment shown in FIG. 1 in a second switching state transmitting the medically relevant data in a wireless manner.

In the second switching state, the changeover switch 11 interrupts the first data line 10 and closes the second data line 12 such that now the communication unit 7 exclusively can access the handover memory 6 and read-out measuring data stored therein. These measuring data are subsequently transmitted in a wireless manner as signal sequence 20 to the second device 2 by the communication unit 7. After read-out of the handover memory 6, the communication unit 7 actuates the changeover switch 11 again in order to transition it back to its first switching state such that the data-generating circuit, i.e. the processor 5 connected to the sensor 3 in the example shown, again can write measuring data to the handover memory 6. Data that have been read-out are marked in the handover memory 6 as read-out or are deleted by the communication unit 7 such that the corresponding memory locations of the handover memory 6 can be over-written.

The handover memory 6 can also be used as main memory by the data-generating circuit and/or the system processor 5. However, it is feasible just as well that the data-generating circuit and/or the system processor can access a separate memory and store in the handover memory only data that is to be exchanged between the data-generating circuit and the communication unit 7.

The transmission of measuring data is triggered in the embodiment shown by a request signal 21 sent by the communication unit 8 of the second device 2. Upon reception of a request signal 21 of this type, the communication unit 7 of the first device 1 actuates the changeover switch 11 in order to be able to read-out the handover memory 6 and then sends the measuring data it has read. Signal sequences sent by the first device 1 and by the second device 2 usually always contain a characteristic code that precludes interference by non-system devices. For transmission, for example packet-oriented protocols, such as Bluetooth, Zigbee, HomeRF, Wibree, NFC, IEEE 802.11 or other protocols, can be used.

Since the changeover switch 11 changes between its switching states without communicating with the data-generating circuit 3, 5 of the first device 1, write operations of the circuit and/or of the microprocessor 5 contained therein might be interrupted and thus disturbed. Error-containing data might be generated in the handover memory 6 as a consequence of an interrupted write operation. In order to prevent these from falsifying the results in a subsequent analysis of the measuring data, the measuring data are combined into data blocks and a data protection sum each is calculated for the data blocks by the microprocessor 5 of the data-generating circuit. In an error-free, non-interrupted write operation, these data blocks are stored in the handover memory 6 together with their corresponding data protection sum. Checking the data protection sum allows determining, at a later time, whether or not a data block stored in the handover memory 6 contains errors. The data protection sum can be checked by the microprocessor of the communication unit 7 such that error-containing data blocks are recognized early and do not need to be sent to the second device 2. However, it is feasible just as well to check the data protection sum in an analytical unit of the second device 2 and to sort-out or correct, to the extent possible, error-containing data blocks only in the second device 2. Preferably, the data protection sum is checked both by the communication unit 7 and by the second device 2. Specific protection sums for the corresponding protocols are added during the transmission process.

In the data transmission system described above, data needed by the data-generating circuit, in particular by the microprocessor 5 contained therein, in the first device 1 can also be transmitted from the second device 2 to the first device 1. Data of this type can, for example, be configuration data, e.g. values of the optimal electrode voltage for the sensor 3 or control commands related to the generation of medically relevant data. The transmission of configuration data of this type from the second device 2 to the first device 1 is called download in order to differentiate this operational mode from transmissions of medically relevant data from the first device 1 to the second device 2 that are called upload. The handover memory 6 shown in FIGS. 5 and 6 has a header 6a, a memory area 6b that is reserved for upload data, and a memory area 6c that is reserved for download data.

Figure 3:
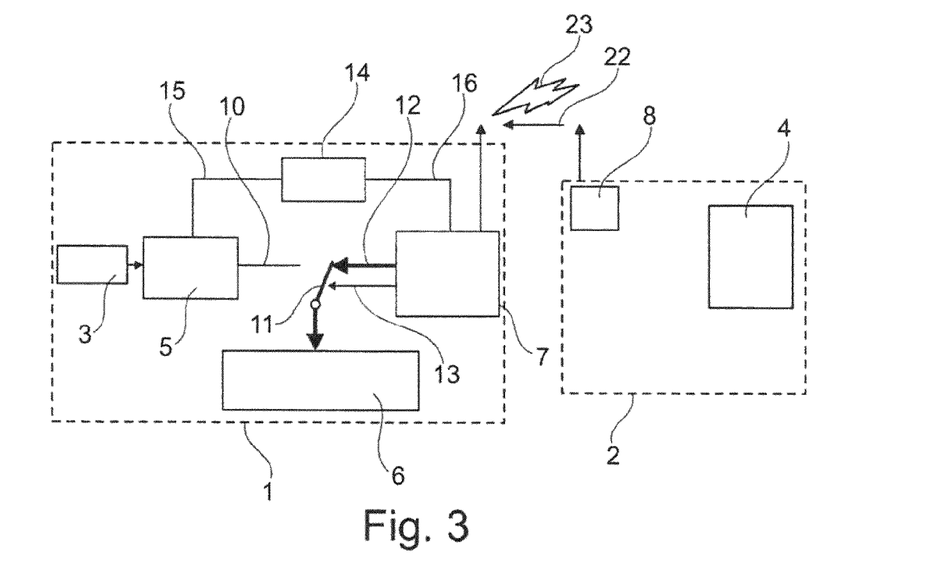
FIG. 3 shows the embodiment shown transmitting configuration data in a wireless manner.

In the download mode that is shown schematically in FIG. 3, the communication unit 8 of the second device 2 initially sends a request signal 22 and, once reception thereof has been confirmed by the communication unit 7 of the first device, data depicted by reference number 23, for example configuration data, intended for the data-generating circuit, i.e. the microprocessor 5 connected to the sensor 3 in the example shown. The communication unit 7 then transitions the changeover switch 11 to the second switching state such that the communication unit 7 can access the handover memory 6 and store the received data therein. Subsequently, the communication unit actuates the changeover switch 11 again in order to return it to its first switching state in which it is connected to the data-generating circuit, i.e. to the microprocessor 5 contained therein. However, it is feasible just as well to set-up the changeover switch 11 such that it returns to its first switching state in a self-actuated manner when the communication unit becomes inactive.

Figure 4:
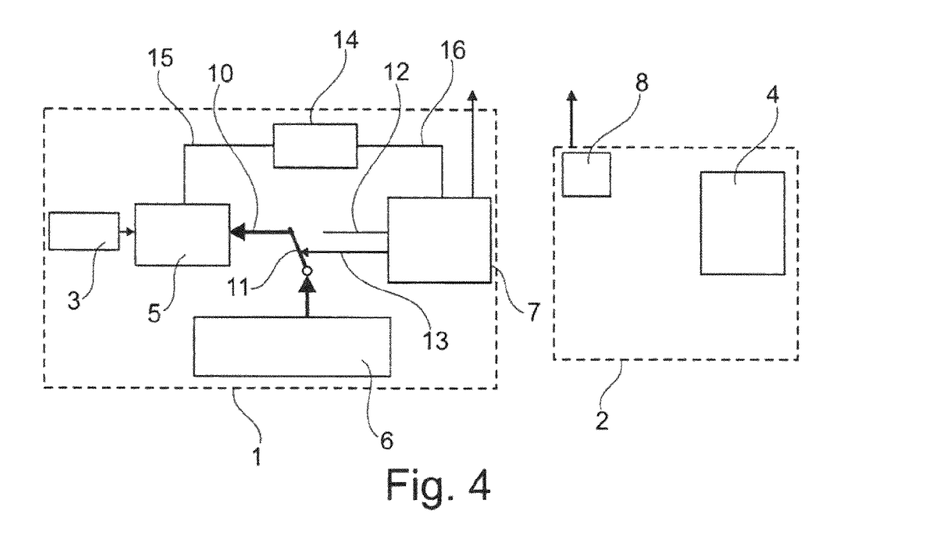
FIG. 4 shows the embodiment shown in a further switching state after transmitting configuration data according to FIG. 3.

Since data are exchanged between the data-generating circuit 3, 5 and the communication unit 7 exclusively via the handover memory 6, the microprocessor 5 of the data-generating circuit is unaware of whether or not new download data have been made available to him in the handover memory 6. For this reason, the microprocessor 5 of the data-generating circuit reads out in fixed time intervals a memory area 6c of the handover memory 6 that has been reserved for configuration and similar data. In order to preclude download data from being read incompletely by the system processor 5, the embodiment shown provides the communication unit 7 to transition the changeover switch 11 again to the second switching state after a completed download no earlier than after a period of time has elapsed that is sufficiently long for the microprocessor 5 to definitely read-out the download area of the handover memory 6 regardless of when the download occurred. The waiting time for which the microprocessor of the communication unit 7 does not actuate the changeover switch 11 after a completed download, can be selected, for example, to be twice as long as the time interval between attempts of the system processor 5 to read-out the download area of the handover memory 6.

Figure 5:
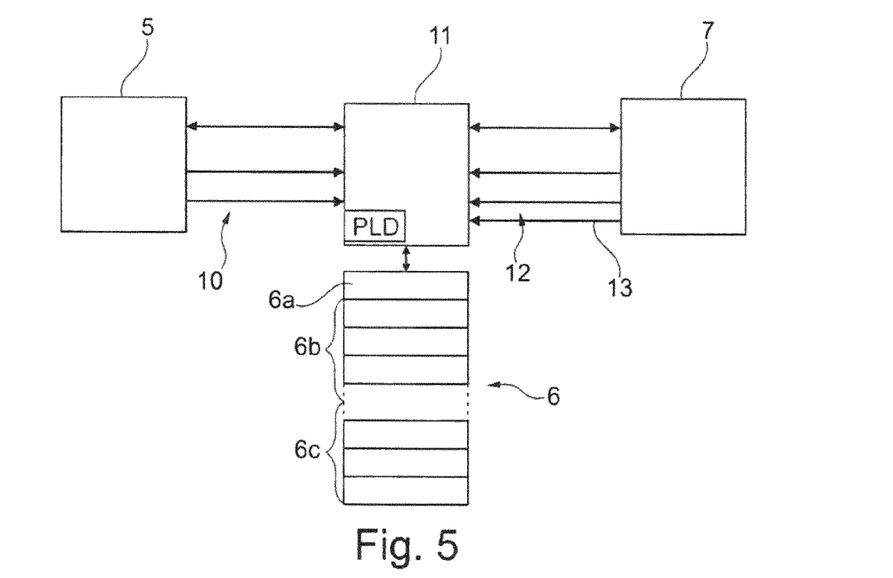
FIG. 5 shows a schematic view of an embodiment of the data bus architecture of the data transmission system shown.
Figure 6:
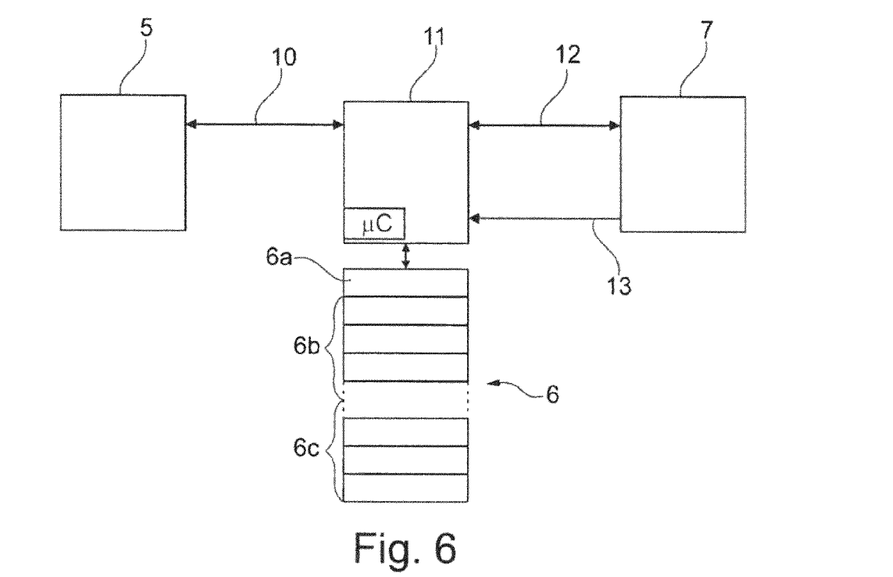
FIG. 6 shows another embodiment of the data bus architecture of the data transmission system shown.

The data lines 10, 12 between the handover memory 6 and the communication unit 7 and/or between the handover memory 6 and the system processor 5 can be structured as parallel busses according to FIG. 5, i.e. consist of multiple single lines, for example approx. 30 data lines. The exemplary embodiment shown provides 8 bit data lines, 16 bit address lines, and 3 bit control lines. In this case it is preferable for the changeover switch 11 to switch all individual lines of a parallel data line of this type. However, it is feasible just as well to provide the data lines 10, 12 between handover memory 6 and communication unit 7 and/or handover memory 6 and system processor 5 in a serial manner. For example SPI or ICC are suitable serial bus systems. If the data lines 10, 12 are provided to be serial, the handover memory 6 can be provided in the form of EEPROM, which would be associated with the advantage of non-volatile temporary memory in case the supply voltage were to be interrupted. However, especially in case the data lines 10, 12 are provided to be parallel, the handover memory can be provided just as well as RAM memory that is particularly advantageous for systems with fast access.

As a matter of principle, the changeover switch 11 can be implemented in the form of a mechanical switch or an electronic switch, for example a transistor switch. Especially if the data lines 10, 12 are provided in the form of parallel busses, the changeover switch can be provided, for example, as ASIC or even as microprocessor or contain a microprocessor. Moreover, another option is to implement the changeover switch with logical circuit components (AND, NAND, OR, NOR, EXOR, latches, etc.) or by means of a freely programmable logical circuit (PLD).

Figure 7:
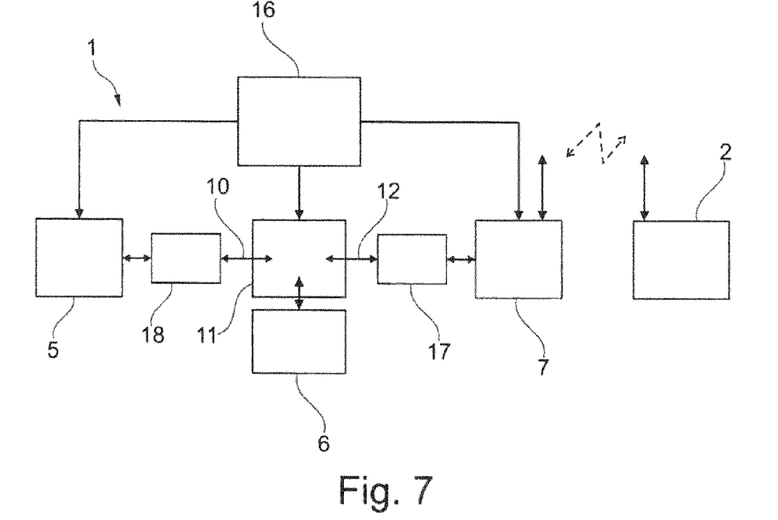
FIG. 7 shows another example of a medical data transmission system.

FIG. 7 shows another embodiment of a medical data transmission system that basically differs from the data transmission system described by means of the preceding figures in that the changeover switch 11 is actuated by a random access processor 17 such that the system processor 5 of the data-generating circuit and the communication unit 7 can access the handover memory 6 in an alternating manner. The time points of switching can be selected freely by the random access processor 17, for example by being predefined by an internal random generator.

The system processor 5 and the communication unit 11 each have access to a temporary memory 17, 18 in which the data intended for the handover memory 6 can be stored temporarily.

Figure 8:
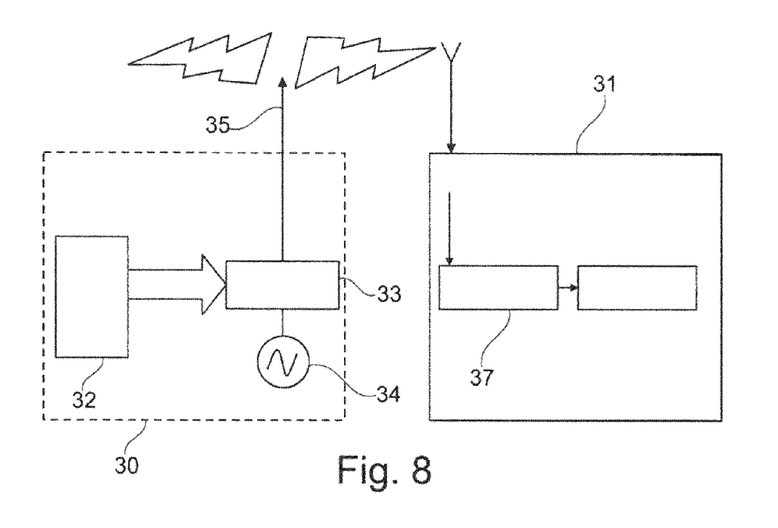
FIG. 8 shows another example of a medical data transmission system.

FIG. 8 shows another embodiment of a medical data transmission system that includes a first device 30 which, according to purpose, is carried on the body by a patient and, in operation, generates medically relevant data that are transmitted to a receiver 37 of a second device 31 in a wireless manner. The first device 30 contains a microprocessor 32 that controls the generation of the medically relevant data and uses an electronic switch 33 to modulate those data, for sending them, onto a carrier frequency that is supplied by a frequency generator 34 and sends the data by means of an antenna 35. These data are received by the second device 31. Since, as a matter of principle, any receiver can receive these data, the data are preferably encoded by the processor 32 of the first device 30 and decoded after reception by a processor 36 of the second device 31.

The sending of the data is unidirectional, i.e. without control pulses being exchanged between the first and the second device. The data can be protected by data protection codes that are calculated for a data packet and allow for checking of whether the data packet has been damaged. Another data protection option is to transmit data packets multiply such that the likelihood of undisturbed reception is increased.

The means described in FIG. 8 initially renders only an upload of data feasible. For downloading, a corresponding backward channel can be created, for example at a different frequency, and is operated in exactly reverse manner.

The procedure for data transmission described by means of FIG. 8 can also be used in the data transmission systems illustrated by means of FIGS. 1 to 7. For example, the data-generating circuit can be provided with a sender by means of which in a special operational mode, for example for test or evaluation purposes, data can be sent in a unidirectional manner.

The procedure for data transmission described above can be used for wire-bound and wire-less, including, for example, optical, data transmission. The changeover switch 11 can likewise be used just as well between the communication unit 8 and the output unit 4 in the device 2. A changeover switch 11 each can be incorporated in both the first and the second device.

Thus, embodiments of the medical data transmission system are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A medical data transmission system, comprising:
a first device which is designed to be worn on a body by a patient and which generates medically relevant data when in operation, said data being transmitted to a second device in a wireless manner,
whereby the first device comprises a communication unit for wireless communication with the second device, a circuit which, in operation, generates medically relevant data, and a handover memory for intermediate storage of data that are to be transmitted from the circuit to the communication unit or from the communication unit to the circuit, and whereby the data-generating circuit is connected to the handover memory via a first data line and the communication unit is connected to the handover memory via a second data line,
characterized in that,
the first device contains a changeover switch that closes the first data line and interrupts the second data line in a first switching state, and interrupts the first data line and closes the second data line in a second switching state, whereby the changeover switch switches between the first and the second switching state without communicating with the data-generating circuit.

2. The medical data transmission system according to claim 1, characterized in that data are exchanged between the data-generating circuit and the communication unit only via the handover memory.

3. The medical data transmission system according to claim 1, characterized in that the changeover switch is actuated by the communication unit.

4. The data transmission system according to claim 1, characterized in that the communication unit contains a microprocessor for controlling the wireless communication with the second device.

5. The data transmission system according to claim 1, characterized in that the data-generating circuit contains a microprocessor for controlling the generation of data.

6. The data transmission system according to claim 1, characterized in that the data-generating circuit contains a sensor which, in operation on or in the body of the patient, measures a medically relevant parameter, in particular an analyte concentration, and stores measuring data of the sensor in the handover memory.

7. The data transmission system according to claim 1, characterized in that the second device has a display facility for displaying measuring results of the sensor.

8. The data transmission system according to claim 1, characterized in that the circuit combines the data it generates into data blocks, calculates a data protection sum each for the data blocks in order to store the data blocks together with the corresponding data protection sum in the handover memory.

9. The data transmission system according to claim 8, characterized in that the communication unit checks the data protection sum of data blocks that are read-out from the handover memory and sends only data blocks that have a correct data sum.

10. A medical data transmission system for transmitting, medical data without the need for synchronization between a first device with an implantable sensor for measuring glucose concentration and a second device for displaying glucose concentrations, comprising:
means for generating medically relevant data by a first device having an implantable sensor for measuring glucose concentrations and a microprocessor which is designed to be worn on a body by a patient;

means for switching into a first switching state that comprises,
   means for connecting a first data line between the microprocessor and handover memory,
   means for interrupting a second data line between the handover memory and a communications unit;

means for writing measuring data from the microprocessor through the first data line to the handover memory;

means for switching into a second switching state upon receiving a request signal that comprises,
   means for interrupting the first data line between the microprocessor and handover memory,
   means for connecting the second data line between the hand over memory and the communications unit means for reading out measurement data by the communicating unit accessing handover memory through the second data line; and, means for transmitting measurement data by the communications unit wirelessly transmitting data to a second device for displaying glucose data.

11. A method for transmitting medical data without the need for synchronization between a first device with an implantable sensor for measuring glucose concentration and a second device for displaying glucose concentrations, comprising:
   generating; medically relevant data by a first device having an implantable sensor for measuring glucose concentrations and a microprocessor which is designed to be worn on a body by a patient;
   switching into a first switching state that comprises,
      connecting a first data line between the microprocessor and handover memory,
      interrupting a second data line between the handover memory and a communications unit;
   writing measuring data from the microprocessor through the first data line to the handover memory;
   switching into a second switching state upon receiving a request signal that comprises,
      interrupting the first data line between the microprocessor and handover memory,
      connecting the second data fine between the handover memory and the communications unit;
   reading out measurement data by the communicating unit accessing handover memory through the second data line; and,
   transmitting measurement data by the communications unit wirelessly transmitting data to a second device for displaying glucose data.

12. The method according to claim 11, further comprising,
   generating the request signal by the second medical device communications unit to request the first medical device communications unit to transmit measurement data to the second medical device to display the medical data;
   transmitting the request signal by the second medical device communications unit to the first medical device communications unit;
   switching into a second switching state that comprises,
      interrupting the first data line between the microprocessor and handover memory,
      connecting the second data line between the handover memory and the communications unit; and,
   transmitting the measurement data from the first medical device communication unit to the second medical device communication unit to display glucose concentrations.

13. The method according to claim 11, further comprising exchanging exclusively medically relevant data from a data generating circuit through handover memory to the first medical device communications unit.

* * * * *